United States Patent [19]

Stednitz

[11] Patent Number: 4,522,200

[45] Date of Patent: Jun. 11, 1985

[54] ADJUSTABLE INTRAMEDULLAR ROD

[75] Inventor: Denis P. Stednitz, Redondo Beach, Calif.

[73] Assignee: ACE Orthopedic Company, Los Angeles, Calif.

[21] Appl. No.: 502,923

[22] Filed: Jun. 10, 1983

[51] Int. Cl.³ ............................................... A61F 5/04
[52] U.S. Cl. .................................................. 128/92 BC
[58] Field of Search ........... 128/92 BC, 92 B, 92 BA, 128/92 R

[56] References Cited

U.S. PATENT DOCUMENTS

| | | | |
|---|---|---|---|
| 887,074 | 5/1908 | Depage | 128/92 B |
| 2,672,861 | 3/1954 | Jonas et al. | 128/92 BC |
| 3,717,146 | 2/1973 | Halloran | 128/92 BC |
| 4,011,602 | 3/1977 | Rybicki et al. | 128/92 B |
| 4,016,874 | 4/1977 | Maffei et al. | 128/92 BC |
| 4,170,990 | 10/1979 | Baumgart et al. | 128/92 BC |
| 4,261,350 | 4/1981 | Branemark et al. | 128/92 BC |
| 4,262,665 | 4/1981 | Roalstad et al. | 128/92 BC |
| 4,275,717 | 6/1981 | Bolesky | 128/92 BC |
| 4,409,974 | 10/1983 | Freedland | 128/92 BC |
| 4,453,539 | 6/1984 | Raftopoulos et al. | 128/92 BC |

Primary Examiner—C. Fred Rosenbaum
Assistant Examiner—C. W. Shedd
Attorney, Agent, or Firm—Hubbard and Stetina

[57] ABSTRACT

An intramedullar rod is formed as a hollow cylinder with slits therein that form a plurality of leaf spring members that bend inward when the rod is inserted into the medullary cavity of the bone.

4 Claims, 4 Drawing Figures

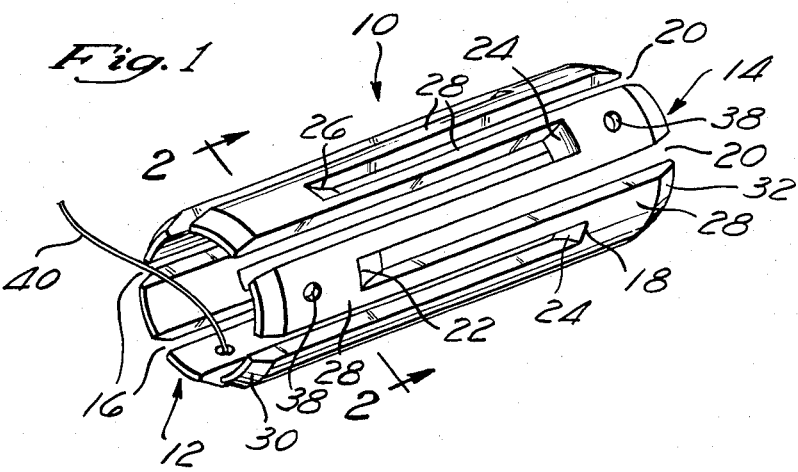
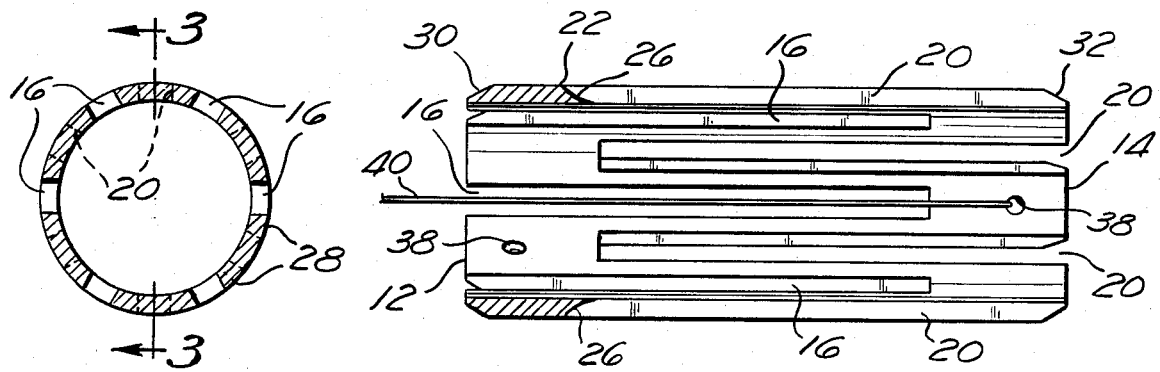
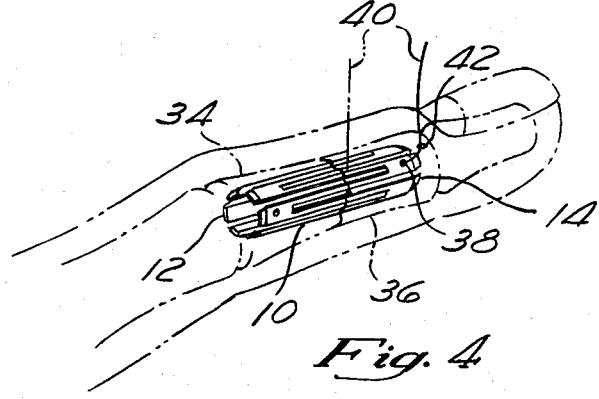

ADJUSTABLE INTRAMEDULLAR ROD

BACKGROUND OF THE INVENTION

The present invention relates generally to apparatus for setting or securing parts of a fractured bone and particularly to apparatus and methods for securing parts of fractured bones such as the phalanges, metacarpals, and metatarsals. Still more particularly, this invention relates to a device for insertion into the medullary cavity of fractured phalanges, metacarpals, and metatarsals to secure the parts together.

It is a known medical procedure to secure the parts of broken bones together by inserting a portion of a rod or tube inside the medullary cavity of one part of the broken bone and then inserting the remainder of the rod or tube inside the medullary cavity of the second portion of the broken bone. Since the phalanges, metacarpals and metatarsals are relatively short bones and, accordingly, difficult to secure with splints or casts, the use of an implanted rod or tube is useful in healing fractures of such bones.

However, a shortcoming of prior techniques for implanting a rod or tube inside the medullary cavity of bones such as the phalanges is the difficulty encountered in securing the rod inside the medullary cavity to retain the fractured portions in contact so that healing may occur.

Prior intramedullar rods generally require drilling of the bone to provide a cavity of suitable shape and dimensions for receiving a rod. Both the rod and the drilled cavity are generally cylindrical so that engagement of the rod in the cavity affords minimal retention against relative axial and rotational movement of the parts of the fractured bone. The necessity of drilling the medullary cavity of the broken bone makes the setting procedure excessively time consuming, which may result in excessive trauma to a patient who has already suffered a serious injury.

SUMMARY OF THE INVENTION

The present invention overcomes the shortcomings of prior intramedullar rods by providing an intramedullar rod having an adjustable diameter. The present invention comprises a hollow intramedullar rod having lengthwise slits formed in the sidewall thereof. Each slit extends from one of the two ends of the rod to a location proximate the other end of the rod with adjacent slits extending from alternating ends of the rod. The slits cause the rod to be radially compressible so that the rod may be inserted into a medullary cavity having a diameter slightly smaller than the normal exterior diameter of the rod. The ends of the rods are preferably tapered to facilitate initiation of insertion of the rod into a medullary cavity having a diameter smaller than the exterior diameter of the rod, and the rod is formed of a material which is sufficiently elastic to exert radially outward forces against the walls of the medullary cavity. The radial force between the rod and the cavity results in formation of frictional forces sufficient to retain the intramedullar rod inside the cavity. Since the geometrical configuration of a rod according to the invention is variable in response to radially applied forces, insertion of the rod into a medullary cavity which is not cylindrical results in retention of the rod against rotation inside the medullary cavity. Therefore, an intramedullary rod according to the invention retains the parts of a broken bone against rotary and axial displacement relative to one another.

A rod according to the invention having particular dimensions is suitable for insertion into medullary cavities of various dimensions less than the exterior diameter of the rod. The rod may be formed in a variety of exterior dimensions depending upon the size of the bone in which the rod is to be inserted.

The present invention may be described as an intramedullar rod for use in orthopedic surgery for setting broken hand and foot bones comprising a single unitary substantially right cylindrical body of biologically compatible resilient metal, having substantially smooth uniform interior and exterior surfaces. The cylinder has first and second ends, and has formed in the cylinder walls at least four slots, and preferably six, or more, at least of two slots extending from the first end more than one-half the distance toward the second end of the cylinder, and at least two of the slots extending from the second end more than one-half the distance toward the first end. The slots, whatever their number, are substantially equally spaced from one another, alternating from the respective ends, and substantially symmetrical about the circumference of the cylindrical body. The cylindrical body is formed of a single piece of resilient metal, and is so configured and constructed as to be compressible diametrically and to exert a resilient force to return toward a predetermined, noncompressed diameter. By reason of this configuration, when the device of this invention is in use, inserted in the medullar cavity of mating ends of the fragments of a fractured bone, the cylindrical body forming the intramedullar rod exerts a constant, resilient force outwardly toward the interior of the fractured bone fragments without the use of expanders or other implements, or fixtures. The intramedullar rod preferably includes at least one apperture formed through the cylinder wall adjacent each of the ends of the cylinder for receiving a suture, thus assisting the surgeon in pulling the intramedullar rod into the fractured bone fragments.

DESCRIPTION OF THE DRAWINGS

FIG. 1 is a perspective view of an adjustable intramedullar rod according to the invention;

FIG. 2 is a cross-sectional view taken along line 2—2 of FIG. 1;

FIG. 3 is a cross-sectional view taken along line 3—3 of FIG. 2; and

FIG. 4 is a perspective view of the invention inserted into the fractured flange to hold the pieces together.

DESCRIPTION OF THE PREFERRED EMBODIMENT

Referring to FIG. 1, an adjustable intramedullar rod 10 according to the invention is preferably formed in a generally cylindrical configuration having a first end 12 and second end 14. The first end 12 has a plurality of slits 16 extending therefrom to points 18 proximate the second end 14. Similarly, the second end 14 has a plurality of slits 20 formed therein extending from the second end 14 to points 22 proximate the first end 12.

Each of the slits 16 preferably terminates at the points 18 with a wedge-shaped portion 24 extending from the points 18 into the corresponding slit 16. As shown in FIGS. 1 and 3, the wedge-shaped portions 24 extend from the points 18 toward the interior of the rod 10. As shown in FIG. 1, the slits 20 terminate at the points 22 with corresponding wedge-shaped portions 26 extending from the points 22 toward the interior of the rod 10. The rod 10 is preferably formed of a material such as titanium or a suitable titanimum alloy, which has elastomeric properties. The portions 28 between adjacent slits 16 and 20 therefore function as leaf springs mounted to the corresponding first and second ends 12 and 14, respectively. The wedge-shaped portions 24 and 26 form smooth transitions between the slits 16 and 20 and the corresponding ends 14 and 12 of the rod 10 provide structural support to the leaf spring portions 28 to prevent the leaf spring portions 28 from breaking off the corresponding end portions 12 and 14.

As shown in FIG. 2, the slots 16 are preferably spaced apart at equal angles around the circumference of the rod 10. A preferred embodiment of the invention has six slots 16 formed in the end 12 and six leaf spring portions 28 at the first end 12. The configuration of the slots 20 and the leaf spring portions 28 at the second end 14 is preferably substantially identical to the configuration of slots 16 and leaf spring portions 28 at the first end 12.

As shown in FIGS. 1-3, the first end 12 has a beveled portion 30 and the second end portion 14 has a beveled portion 32. The beveled portions 30 and 32 facilitate insertion of the rod 10 to the medullary cavities of fractured bones. The rod 10 is preferably formed of titanium or a titanium alloy but may also be formed of any other suitable metal, such as stainless steel, or of plastic. The rod 10 may have dimensions suitable for the particular bone to be set. It has been found that diameters of 3, 5 and 7 mm. and lengths ranging from approximately 5 to 20 mm. give satisfactory results for many different bones in a human body.

When the beveled portion 30 of the first end 12 is inserted into a medullary cavity having a diameter slightly smaller than the exterior diameter of the rod 10, the rod 10 is compressed radially inward to conform to the size and configuration of the medullary cavity. The material from which the rod 10 is formed must be sufficiently elastic to cause the leaf spring members 28 to exert radially outward forces against the walls of the medullary cavity to form frictional forces to retain the rod 10 against undesired axial movement within the medullary cavity. Since the medullary cavities of most human bones have irregular rather than circular cross-sections, the plurality of leaf spring portions 28 causes the configuration of the rod 10 to adjust in accordance with the cross-sectional configuration of the medullary cavity. For example, some bones have medullary cavities having D-shaped cross sections. In such bones, the rod 10 conforms to the D-shaped configuration of the cross-section of the medullary cavity, with the result being that the leaf spring members 28 engage the walls of the medullary cavity to retain the rod 10 against rotation within the medullary cavity.

In order to promote healing of a fracture, it is necessary that the two bone portions be placed as closely as possible in their natural alignment and retained against axial and rotational movement relative to one another. To set some fractures, it is possible to insert the first end 12 into the medullary cavity of a first bone portion 34 shown in FIG. 4, with the second end 14 of the rod 10 extending from the first bone portion 34. The second bone portion 36 is then properly aligned and axially moved toward the second bone segment to insert the second end 14 of the rod 10 into the medullary cavity of the second bone portion 36.

Still referring to FIG. 4, after the second end 14 is inserted into the second bone portion 36, the rod 10 conforms to the medullary cavities of both the first bone portion 34 and second bone portion 36 to retain them against both axial movement and rotation relative to one another. In certain applications, it may be necessary to insert substantially all of the rod 10 into the medullary cavity of the first bone portion 34 and then to pull the second end portion 14 of the rod 10 into the medullary cavity of a second bone portion 36. Referring to FIGS. 1 and 3, alternate leaf spring members 28 at each of the first and second ends, respectively, include a passage 38 therethrough for insertion of a suture 40. The suture 40, which may be a string-like member, is attached, for example, to the first end 12 at one of the passages 38. The first end 12 of the rod 10 is then inserted into the medullary cavity of the first bone portion 34 a distance sufficient to permit proper alignment of the second bore portion with the first bone portion 34. When the bone portions 34 and 36 are properly aligned, the bone portion 36 is urged toward the bone portion 34 to insert any portion of the second end 14 of the rod 10 which may be extending from the medullary cavity of the bone portion 34 into the medullary cavity of the bone portion 36. The suture 40 may extend out of the fractured region through one of the slots 16 or 20 as shown in FIG. 4. An orthopedist setting a fractured bone using this technique would then exert a force on the suture 40 to partially pull the rod 10 out of the medullary cavity of the first bone portion 34 so that the second end 14 of the rod 10 projects a distance into the medullary cavity of the second bone portion 36 sufficient to stabilize the bone portions 34 and 36 for healing.

The suture 40 may also extend out of the bone through one of the passages 38 adjacent the end portion 14 and a hole 42 into the intramedullar cavity of the bone portion 36. The suture 40 is then drawn through the hole 42 and the bone portion 36 a distance sufficient to attach an end of the suture 40 to a passage 38 adjacent the end 12, which is to be inserted into the intramedullar cavity of the bone portion 34. The end 12 is then inserted into the bone portion 34 a distance sufficient to permit placement of the second bone portion 36 over the end 14 of rod 10. The bone portions 34 and 36 are then properly aligned and the orthopedist exerts a force on the end of the suture 40 that projects from the hole 42 in the second bone portion 36 to pull the rod 10 out of the bone portion 34 and into the bone portion 36 a distance sufficient to stabilize the bone portions 34 and 36 for healing the fracture.

What is claimed is:

1. An intramedullar rod for use in orthopedic surgery for setting broken hand and foot bones comprising a single unitary substantially right cylindrical body of biologically compatible resilient metal, having substantially smooth uniform interior and exterior surfaces, the cylinder having first and second ends and having formed in the cylinder walls at least four slots, at least two of said slots extending from the first end more than one-half the distance toward the second end, and two of said slots extending from the second end more than one-half the distance toward the first end, the slots being substantially equally spaced from one another alternating from the respective ends substantially symmetrically about the circumference of the cylindrical body, the cylindrical body being formed of a single piece of resilient metal, and being so configured and constructed as to be compressible diametrically, and to exert a resilient force to return toward a predetermined noncompressed diameter, whereby when in use inserted in the medullar cavity of mating ends of a fractured bone, the cylindrical body exerts a constant, resilient force outwardly against the interior of such fractured bone without the use of other implements.

2. The intramedullar rod of clam 1, wherein at least one aperture is formed through the cylinder wall adjacent each end of the cylinder for receiving a suture for assisting in pulling the intramedullar rod into the fractured bone fragments during insertion.

3. The intramedullar rod of claim 2, wherein the cylinder has formed therein at least three slots extending from each end thereof.

4. The intramedullar rod of claim 1, wherein the cylinder has formed therein at least three slots extending from each end thereof, and wherein the exterior ends of the cylinder are chamfered to facilitate entry into the medullar cavity.

* * * * *